US010317337B2

(12) United States Patent
Price et al.

(10) Patent No.: US 10,317,337 B2
(45) Date of Patent: Jun. 11, 2019

(54) REVERSE DESIGN TECHNIQUE FOR OPTICAL PROCESSING ELEMENTS

(71) Applicant: HALLIBURTON ENERGY SERVICES, INC., Houston, TX (US)

(72) Inventors: James M. Price, The Woodlands, TX (US); Aditya B. Nayak, Houston, TX (US); Bin Dai, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 12 days.

(21) Appl. No.: 15/523,871

(22) PCT Filed: May 27, 2016

(86) PCT No.: PCT/US2016/034521
§ 371 (c)(1),
(2) Date: May 2, 2017

(87) PCT Pub. No.: WO2017/204814
PCT Pub. Date: Nov. 30, 2017

(65) Prior Publication Data
US 2018/0202922 A1 Jul. 19, 2018

(51) Int. Cl.
G01N 21/27 (2006.01)
G01J 3/02 (2006.01)
(Continued)

(52) U.S. Cl.
CPC ......... G01N 21/274 (2013.01); E21B 47/123 (2013.01); E21B 49/08 (2013.01);
(Continued)

(58) Field of Classification Search
CPC . G01N 21/276; G01N 21/274; G02B 27/0012
See application file for complete search history.

(56) References Cited

U.S. PATENT DOCUMENTS 5,397,899 A * 3/1995 DiFoggio ............... G01N 21/35
250/339.09
6,584,413 B1 * 6/2003 Keenan .................... G01J 3/28
702/194
(Continued)

FOREIGN PATENT DOCUMENTS

WO WO-2014/112974 A1 7/2014
WO WO-2014/130025 A1 8/2014
(Continued)

OTHER PUBLICATIONS

International Search Report and Written Opinion from International Application No. PCT/US2016/034521, dated Feb. 21, 2017.

Primary Examiner — Kara E. Geisel
Assistant Examiner — Maurice C Smith
(74) Attorney, Agent, or Firm — Gilliam IP PLLC

(57) ABSTRACT

A method for designing an integrated computational element (ICE) includes generating an array of discrete data points and plotting the discrete data points across a predetermined wavelength region. A line shape is then generated that connects to and is constrained by the array of discrete data points, and thereby generates a first transmission function. The discrete data points are then iteratively modified based on one or more performance criteria to generate a second transmission function. A model transmission function corresponding to a model ICE design is then fitted to the second transmission function to identifying a predictive ICE design configured to detect a desired characteristic of interest.

20 Claims, 3 Drawing Sheets

(51) Int. Cl.
    *G02B 27/00*    (2006.01)
    *E21B 47/12*    (2012.01)
    *E21B 49/08*    (2006.01)
    *G01J 3/28*    (2006.01)
    *G01N 21/31*    (2006.01)

(52) U.S. Cl.
    CPC ............... *G01J 3/02* (2013.01); *G01J 3/0294* (2013.01); *G01J 3/28* (2013.01); *G01N 21/31* (2013.01); *G02B 27/0012* (2013.01)

(56) References Cited

U.S. PATENT DOCUMENTS

| | | | |
|---|---|---|---|
| 7,138,156 B1* | 11/2006 | Myrick | G02B 5/285 427/10 |
| 8,780,352 B2 | 7/2014 | Freese et al. | |
| 8,823,939 B2 | 9/2014 | Freese et al. | |
| 8,879,053 B2 | 11/2014 | Freese et al. | |
| 8,912,477 B2 | 12/2014 | Freese et al. | |
| 8,941,046 B2 | 1/2015 | Freese et al. | |
| 9,019,501 B2 | 4/2015 | Freese et al. | |
| 9,029,761 B2* | 5/2015 | Jones | G01N 27/72 250/253 |
| 9,074,990 B2 | 7/2015 | Freese et al. | |
| 9,097,649 B2* | 8/2015 | Simcock | G06F 17/50 |
| 9,103,716 B2 | 8/2015 | Tunheim et al. | |
| 9,103,767 B2 | 8/2015 | Freese et al. | |
| 2009/0219512 A1 | 9/2009 | Myrick et al. | |
| 2013/0284894 A1 | 10/2013 | Freese et al. | |
| 2013/0284895 A1 | 10/2013 | Freese et al. | |
| 2014/0110105 A1 | 4/2014 | Jones et al. | |
| 2014/0255598 A1 | 9/2014 | Simcock et al. | |
| 2015/0205000 A1 | 7/2015 | Perkins et al. | |
| 2015/0234976 A1 | 8/2015 | Chen et al. | |
| 2015/0277438 A1 | 10/2015 | Chen et al. | |
| 2015/0300945 A1 | 10/2015 | Gao et al. | |

FOREIGN PATENT DOCUMENTS

| | | |
|---|---|---|
| WO | WO-2014/137354 A1 | 9/2014 |
| WO | WO-2015/034468 A1 | 3/2015 |
| WO | WO-2015/060816 A1 | 4/2015 |
| WO | WO-2015/084303 A1 | 6/2015 |
| WO | WO-2015/084351 A1 | 6/2015 |
| WO | WO-2015/099671 A1 | 7/2015 |
| WO | WO-2015/099706 A1 | 7/2015 |
| WO | WO-2015/126386 A1 | 8/2015 |
| WO | WO-2015/133998 A1 | 9/2015 |
| WO | WO-2015/134036 A1 | 9/2015 |
| WO | WO-2015/142353 A1 | 9/2015 |
| WO | WO-2015/171149 A1 | 11/2015 |

* cited by examiner

REVERSE DESIGN TECHNIQUE FOR OPTICAL PROCESSING ELEMENTS

BACKGROUND

Optical computing devices, also commonly referred to as "opticoanalytical devices," can be used to analyze and monitor a sample substance in real time. Such optical computing devices will often employ a light source that emits electromagnetic radiation that reflects from or is transmitted through the sample and optically interacts with an optical processing element to determine quantitative and/or qualitative values of one or more physical or chemical properties of the substance being analyzed. The optical processing element may be, for example, an integrated computational element ("ICE"). One type of ICE is an optical thin film interference device, also known as a multivariate optical element ("MOE"). Each ICE can be designed to operate over a continuum of wavelengths in the electromagnetic spectrum from the vacuum-UV to infrared (IR) ranges, or any sub-set of that region. Electromagnetic radiation that optically interacts with the sample substance is changed and processed by the ICE so as to be measured by a detector. The output of the detector can be correlated to a physical or chemical property of the substance being analyzed.

A traditional ICE includes first and second pluralities of optical thin film layers consisting of various materials whose index of refraction and size (e.g., thickness) varies between each layer. An ICE design refers to the substrate, number and thickness of the respective layers of the ICE, and the complex refractive indices of the layers. The complex refractive index includes both the real 'n' and imaginary 'k' components of the refractive index. The layers are strategically deposited and sized so as to selectively pass predetermined fractions of electromagnetic radiation at different wavelengths configured to substantially mimic a regression vector corresponding to a particular physical or chemical property of interest of a substance of interest. Accordingly, an ICE design will exhibit a transmission function (spectrum) that is weighted with respect to wavelength. As a result, the output light intensity from the ICE conveyed to the detector may be related to the physical or chemical property of interest for the substance.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
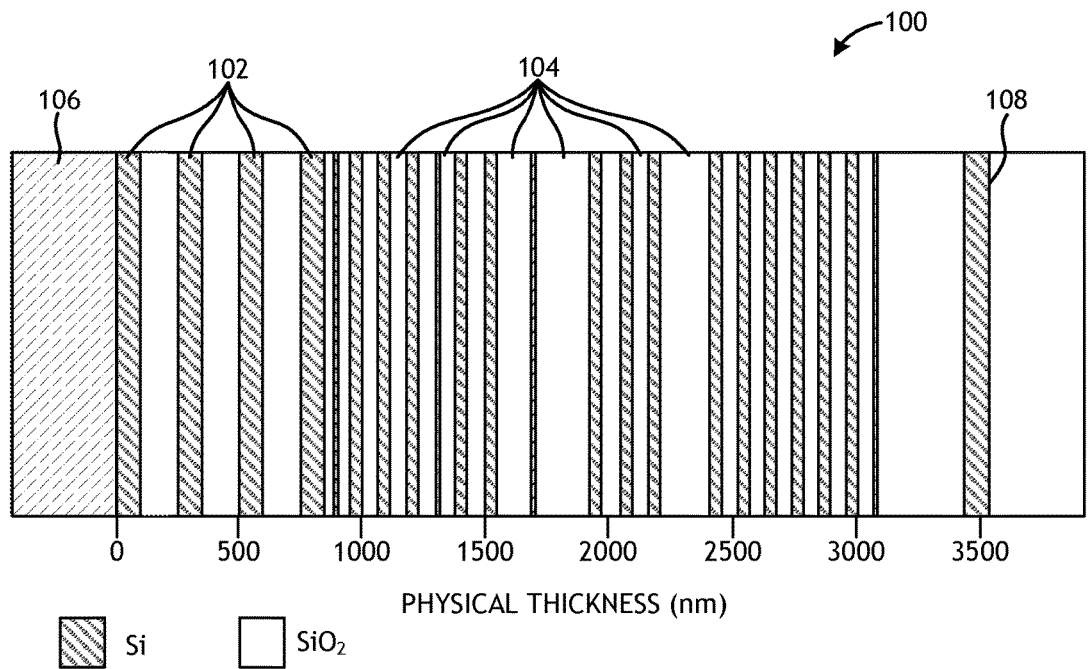
FIG. 1 is a cross-sectional view of an exemplary integrated computational element.

The present invention relates to optical processing elements and, more particularly, to improved techniques for the design of optical processing elements for use in optical computing devices.

The present disclosure expands the design palate for optical processing elements, such as Integrated computational elements ("ICEs"), for use in optical computing devices. According to the improved methods described herein, an array of discrete data points are generated and plotted across a predetermined wavelength region. A line shape is then generated and is constrained by the array of discrete data points, which results in the generation of a first transmission function. The discrete data points may then be iteratively modified based on one or more performance criteria to generate a second transmission function. A model transmission function corresponding to a model ICE design may then be fitted to the second transmission function to identify a predictive ICE design configured to detect a desired characteristic of interest.

The methods disclosed herein may prove advantageous in the design, evaluation, and fabrication of optical processing elements (e.g., ICEs) that may be used in the oil and gas industry, such as for monitoring and detecting oil/gas-related substances (e.g., hydrocarbons, drilling fluids, completion fluids, treatment fluids, etc.). The ICEs designed using the methods disclosed herein may equally be used in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "characteristic" or "characteristic of interest" refers to a chemical, mechanical, or physical property of a substance to be analyzed or a sample of the substance. The characteristic of a substance may include a quantitative or qualitative value of one or more chemical constituents or compounds present therein or any physical property associated therewith. Such chemical constituents and compounds may be referred to herein as "analytes". Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from an optical processing element (e.g., an integrated computational element) or a substance being analyzed with the help of the optical processing element. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an integrated computational element (ICE). The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art.

As indicated above, the present disclosure provides or otherwise describes improved methods for designing optical processing elements, such as ICEs, for use in optical computing devices. In operation, an ICE is capable of distinguishing electromagnetic radiation related to a characteristic of interest of a substance from electromagnetic radiation related to other components of the substance.

FIG. 1 is a cross-sectional view of an exemplary ICE 100. As illustrated, the ICE 100 includes a plurality of alternating thin film layers shown as layers 102 and 104. The first layers 102 are made of a material that exhibits a high index of refraction, such as silicon (Si), and the second layers 104 are made of a material that exhibits a low index of refraction, such as quartz ($SiO_2$). Other examples of materials that might be used include, but are not limited to, niobia and niobium, germanium and germania, MgF, SiO, and other high and low index materials generally known in the art. The layers 102, 104 are strategically deposited on an optical substrate 106, such as BK-7 optical glass. In other embodiments, the substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE 100 depicted in FIG. 1 does not in fact represent an ICE configured to detect any specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 exhibit different complex refractive indices, where the complex refractive index includes both real 'n' and imaginary 'k' components of the refractive index. By properly selecting the materials of the layers 102, 104 and their relative thickness and spacing, the ICE 100 will be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE 100 is configured to perform the dot product of the received electromagnetic radiation and the wavelength dependent transmission function (spectrum) of the ICE 100. The wavelength dependent transmission function of the ICE 100 is dependent on the substrate 106, the material refractive index of each layer 102, 104, the number of layers 102, 104 and thickness of each layer 102, 104. As a result, the output light intensity of the ICE 100 is related to the characteristic or analyte of interest.

As further explanation, accurately determining the regression vector of the characteristic of interest in the sample substance provides a means for an optical computing device to determine or otherwise calculate a concentration of said characteristic in the sample substance. The regression vector for each characteristic may be determined using standard procedures that will be familiar to one having ordinary skill in the art. For example, analyzing the spectrum of the sample substance may include determining a dot product of the regression vector for each characteristic of the sample substance being analyzed. As one of ordinary skill will recognize, a dot product of a vector is a scalar quantity (i.e., a real 'n' number). While the dot product value is believed to have no physical meaning by itself (e.g., it may return a positive or negative result of any magnitude), comparison of the dot product value of a sample substance with dot product values obtained for known reference standards and plotted in a calibration curve allows the dot product value of the sample substance to be correlated with a concentration or value of a desired characteristic, thereby allowing unknown sample substances to be accurately analyzed.

To determine the dot product, one multiples the regression coefficient of the regression vector at a given wavelength by the spectral intensity at the same wavelength. This process is repeated for all wavelengths analyzed, and the products are summed over the entire wavelength range to yield the dot product. Two or more characteristics may be determined from a single spectrum of the sample substance by applying a corresponding regression vector for each characteristic.

In practice, it is possible to derive information from electromagnetic radiation interacting with a sample substance by, for example, separating the electromagnetic radiation from several samples into wavelength bands and performing a multiple linear regression of the band intensity against a characteristic of interest determined by another measurement technique for each sample substance. The measured characteristic may be expressed and modeled by multiple linear regression techniques that will be familiar to one having ordinary skill in the art. Specifically, if y is the measured value of the concentration or characteristic, y may be expressed as in Equation 1:

$$y = a_0 + a_1 w_1 + a_2 w_2 + a_3 w_3 + a_4 w_4 + \quad \text{Equation (1)}$$

where each 'a' is a constant determined by the regression analysis and each 'w' is the light intensity for each wavelength band. Depending on the circumstances, the estimate obtained from Equation (1) may be inaccurate, for example, due to the presence of other characteristics within the sample substance that may affect the intensity of the wavelength bands. A more accurate estimate may be obtained by expressing the electromagnetic radiation in terms of its principal components.

To obtain the principal components, spectroscopic data is collected for a variety of similar sample substances using the same type of electromagnetic radiation. For example, following exposure to each sample substance, the electromagnetic radiation may be collected and the spectral intensity at each wavelength may be measured for each sample substance. This data may then be pooled and subjected to a linear-algebraic process known as singular value decomposition (SVD) in order to determine the principal components. Use of SVD in principal component analysis will be well understood by one having ordinary skill in the art. Briefly, however, principal component analysis is a dimension reduction technique that takes 'm' spectra with 'n' independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. Normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Equation (2):

$$x_1 z_1 + x_2 z_2 + \ldots + x_n z_n \quad \text{Equation (2)}$$

The scalar multipliers $x_n$ may be considered the "magnitudes" of the principal components in a given electromagnetic radiation sample when the principal components are understood to have a standardized magnitude as provided by normalization.

Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Moreover, because the principal components are orthogonal to each other, the dot product of any principal component with any other principal component is zero. Physically, this means that the components do not spectrally interfere with each other. If data is altered to change the magnitude of one component in the original electromagnetic radiation signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude, whether positive or negative.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of the characteristic of the sample substance based upon the information carried by the electromagnetic radiation that has interacted with that sample substance. Differences observed in spectra of sample substances having varying quantities of an analyte or values of a characteristic may be described as differences in the magnitudes of the principal components. Thus, the concentration of the characteristic may be expressed by the principal components according to Equation (3) in the case where four principal components are used:

$$y = a_0 + a_1 x_1 + a_2 x_2 + a_3 x_3 + a_4 x_4 \quad \text{Equation (3)}$$

where 'y' is a concentration or value of a characteristic, each a is a constant determined by the regression analysis, and $x_1$, $x_2$, $x_3$ and $x_4$ are the first, second, third, and fourth principal component magnitudes, respectively. Equation (3) may be referred to as a regression vector. The regression vector may be used to provide an estimate for the concentration or value of the characteristic for an unknown sample.

Regression vector calculations may be performed by a computer based on spectrograph measurements of electromagnetic radiation by wavelength. The spectrograph system spreads the electromagnetic radiation into its spectrum and measures the spectral intensity at each wavelength over the wavelength range. Using Equation (3), the computer reads the intensity data and decomposes the electromagnetic radiation sample into the principal component magnitudes $x_n$ by determining the dot product of the total signal with each component. The component magnitudes are then applied to the regression equation to determine a concentration or value of the characteristic.

To simplify the foregoing procedure, however, the regression vector can be converted to a form that is a function of wavelength so that only one dot product is determined. Each normalized principal component vector $z_n$ has a value over all or part of the total wavelength range. If each wavelength value of each component vector is multiplied by the regression constant and corresponding to the component vector, and if the resulting weighted principal components are summed by wavelength, the regression vector takes the form of Equation (4):

$$y = a_0 + b_1 u_1 + b_2 u_2 + \ldots + b_n u_n \quad \text{Equation (4)}$$

where $a_0$ is the first regression constant from Equation (3), $b_n$ is the sum of the multiple of each regression constant $a_n$ from Equation (3) and the value of its respective normalized regression vector at wavelength 'n', and $u_n$ is the intensity of the electromagnetic radiation at wavelength 'n'. Thus, the new constants define a vector in wavelength space that directly describes a concentration or characteristic of a sample substance. The regression vector in the form of Equation (4) represents the dot product of an electromagnetic radiation sample with this vector.

Normalization of the principal components provides the components with an arbitrary value for use during the regression analysis. Accordingly, it is very unlikely that the dot product value produced by the regression vector will be equal to the actual concentration or characteristic value of a sample substance being analyzed. The dot product result is, however, related (e.g., proportional or having a logarithmic or exponential relationship) to the concentration or characteristic value. As discussed above, the relationship may be determined by measuring one or more known calibration samples by conventional means and comparing the result to the dot product value of the regression vector. Thereafter, the dot product result can be compared to the value obtained from the calibration standards in order to determine the concentration or characteristic of an unknown sample being analyzed.

Before an ICE (i.e., the ICE 100 of FIG. 1) is physically fabricated for use, the ICE must be designed to be predictive of a desired characteristic or analyte of interest of a substance being analyzed. One methodology used to design and fabricate an ICE is commonly referred to as the "forward design process." In the forward design process, several (e.g., 100,000+) random designs of the ICE are generated using a computer-based software program or "design suite." The design suite is stored on a computer-readable medium containing program instructions configured to be executed by one or more processors of a computer system. Ultimately, the design suite generates a theoretical ICE design for each of the 100,000+ random designs, each being optimized and otherwise configured to detect a particular characteristic of interest of a substance desired to be analyzed.

The design suite commences the design process by generating a single random ICE design having a random number of layers (i.e., layers 102, 104 of FIG. 1) and/or a random thickness for each layer. The resulting random ICE design yields a given transmission spectrum (function), which is intended to match or closely mimic a regression vector having a series of peaks and valleys that are co-related to the desired characteristic of interest. The performance of this random ICE design is then determined by calculating one or more performance criteria (alternately referred to as "figures of merit") associated with the random ICE design as compared with a known or measured analyte concentration of an optical data set corresponding to the desired characteristic of interest. Example performance criteria include, but are not limited to, standard error of calibration (SEC), standard error of prediction (SEP), calibration sensitivity, transmission throughput, minimum prediction error, slope of the calibration curve, signal-to-noise ratio, environmental performance characteristics, predictive concentration range, linearity of prediction, thin-film stack thickness, individual layer thicknesses, mean transmission value, variability of the above performance criteria as a function of temperature or fabrication tolerance, corresponding to the particular characteristic of interest.

In some forward design processes, the performance of the random ICE design may be based on its calculated SEC (alternately referred to as "accuracy"), which is indicative of how predictive the particular ICE will be for the characteristic of interest during use. The SEC is generally calculated from a set of test data obtained through the projected transmission spectrum (function) of the random ICE design and comparing a predicted result of the characteristic of interest for each sample in the test set to that of a known value for the characteristic of interest. It should be noted, however, that the sensitivity of the random ICE design may equally be calculated from the encoded ICE regression vector and evaluated for predictability. Sensitivity can be determined by determining the detector response for the given ICE transmission function and then plotting this detector response vs. the analyte concentration. The slope of this plot determines the sensitivity, and the ICE is designed with the aim of maximizing this slope.

The design suite then proceeds to iteratively modify the initial random ICE designs in an attempt to change the transmission function and thereby improve one or more of the performance criteria. Such modifications of the random ICE designs that result in changes to the transmission function include varying layer optical thicknesses and/or adding or removing layers to the thin film stack. Such iterations are typically small or minute changes to the random ICE design, such as altering the thickness of a single layer by as little as 0.01 nanometers (nm). The result is the generation of a theoretical ICE design that approaches one or more minimum performance criteria for predicting the characteristic of interest. The design suite repeats this process of optimizing the random ICE designs to produce tens of thousands of theoretical designs. In some cases, the design suite may end up producing 100,000+ theoretical ICE designs from each original random ICE design.

Once these optimized (theoretical) ICE designs are generated, they are then sorted by the design suite based on the various performance criteria described above, such as prediction error and signal. In some cases, the theoretical ICE designs may be sorted based on their overall SEC (accuracy) as tested against a known value for the characteristic of interest. The SEC for each theoretical ICE design may be calculated by taking the square root of the sum of squares between the known value for the characteristic of interest and the predicted value as derived from the transmission function of the particular theoretical ICE design. This is accomplished for each theoretical ICE design by calculating its respective transmission function and applying that transmission function to the known data set of the analyte of interest.

In some cases, the design suite may be configured to iterate and/or optimize layer thicknesses and numbers until reaching a reasonable SEC for one or more of the theoretical ICE designs. In some embodiments, ICE designs exhibiting an SEC of 2.00 or less, for example, may be considered "predictive" or "viable" and ICE designs exhibiting an SEC of greater than 2.00 may be considered "non-predictive." Those ICE designs that are ultimately considered non-predictive may be removed from consideration either by an operator or by software instructions carried out by the design suite.

Once a predictive ICE design is ultimately selected for fabrication from the theoretical ICE designs, the predictive ICE design may then be loaded into a fabrication computer program configured to instruct an associated fabrication machine or module to physically manufacture the ICE. The fabrication computer program may be configured to receive and/or download the specifications for the predictive ICE design from the design suite and instruct the fabrication machine to physically create a corresponding ICE by methodically or sequentially depositing the various layers of the ICE to the specified layer thicknesses.

Since the forward design process starts with an extremely large set of random ICE designs (e.g., 100,000+ designs), and each random ICE design is iteratively optimized as described above, it requires immense computational capacity and time to generate predictive ICE designs suitable for fabrication. Moreover, the forward design process can produce several optimized ICE designs that are substantially identical, thereby resulting in wasted calculation time for non-unique ICE designs.

The present disclosure provides novel methods for the design and fabrication of an ICE. More particularly, the exemplary methods described herein employ a "reverse design process" in which an ICE transmission function (spectrum) is optimized irrespective of any thin film stack parameters (i.e., number of layers, layer thickness, etc.). This offers a distinctive advantage over the forward design process by allowing the ICE design to evolve without becoming trapped in a local minimum constrained by Fresnel equations and/or fabrication conditions that affect the material properties of a fabricated ICE.

Figure 2:
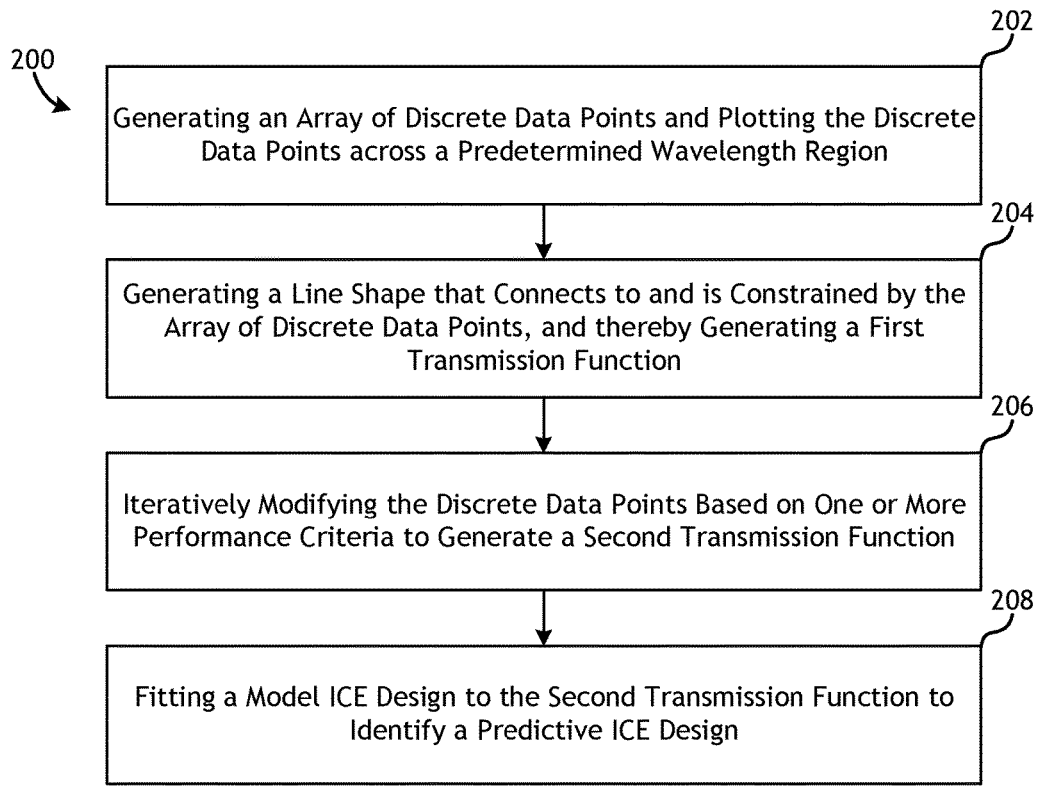
FIG. 2 is a schematic flowchart of an exemplary method of designing an integrated computational element using a reverse design process.

FIG. 2 is a schematic flowchart of an exemplary method 200 of designing an ICE using a reverse design process, according to one or more embodiments. The resulting predictive ICE designs derived through the method 200 may be similar in some respects to the ICE 100 of FIG. 1, but may be generated faster and computationally less expensive as compared to ICEs designed using the forward design process. As illustrated, the method 200 may first include generating an array of discrete data points and plotting the discrete data points across a predetermined wavelength region, as at 202. The predetermined wavelength region may correspond to a wavelength range where a desired characteristic of interest may be detected (measured), and the magnitude of each discrete data point may be randomly or selectively assigned a transmittance value ranging between zero and 1.

Figure 3:
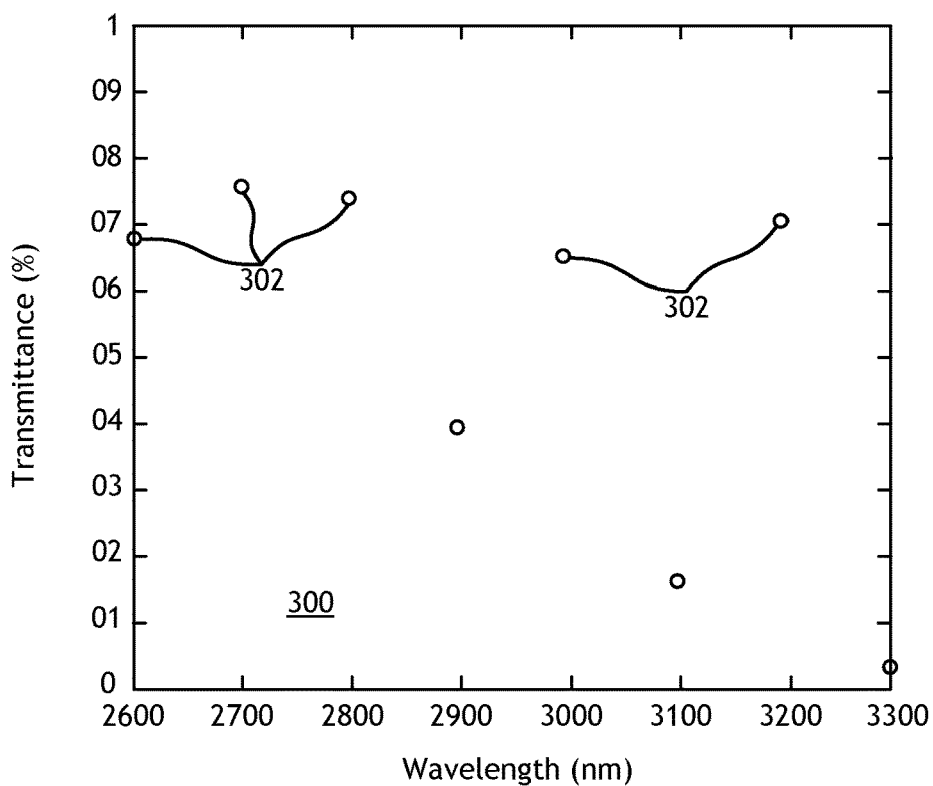
FIG. 3 is an example transmittance versus wavelength plot showing an array of discrete data points plotted along a predetermined wavelength region.

FIG. 3 is an example transmittance versus wavelength plot 300 showing an array of discrete data points 302 plotted along a predetermined wavelength region ranging from 2600 nm to 3300 nm. The plot 300 may be generated as a result of step 202 of the method 200 of FIG. 2. The wavelength region 2600-3300 nm in the plot 300 may correspond to, for example, the wavelength region where carbon dioxide ($CO_2$) is detectable or measureable. Each discrete data point 302 is assigned (randomly or selectively) a magnitude constrained between zero and 1 that corresponds to a transmittance value (percentage) for the particular data point. It should be noted that the array of discrete data points 302 do not represent any particular ICE design or ICE application, but is provided for illustrative purposes only in describing the aspects of the present disclosure.

The array of discrete data points 302 may be generated using a computer-operated random number generator. The random number generator may be operated by MATLAB® or a similar software program having instructions capable of being executed by a computer. The random number generator may be programmed to select a finite number of discrete data points 302 and randomly project (place) the data points 302 within the predetermined wavelength region and constrained to a value between zero and 1. While it is theoretically possible to select and randomly project hundreds or even thousands of discrete data points 302, it may be infeasible or inefficient to do so. Accordingly, the random number generator may be programmed with an upper limit parameter to the number of allowable data points 302. Theoretically, the upper limit for the total number of data points 302 may be any number, but would include at least one data point 302. Accordingly, the random number generator may be configured to limit the number of allowable data points 302 to a range between 1 and n−1, where n is the number of wavelength data points. In the illustrated embodiment, for example, eight data points 302 were generated and were plotted at 100 nm increments from each other and randomly assigned a transmittance magnitude ranging between zero and 1.

In other embodiments, however, the array of discrete data points 302 may be determined based on critical point values for a pre-determined regression vector corresponding to a character of interest. The critical point values (extrema) may be obtained by identifying one or more extrema of the predetermined regression vector corresponding to the characteristic of interest. The resulting data points may then be unequally spaced over the predetermined wavelength region and assigned a transmittance magnitude ranging between zero and 1. The predetermined regression vector may be determined from a multivariate regression model, such as partial least squares (PLS) or principal components regression (PCR).

Figure 4:
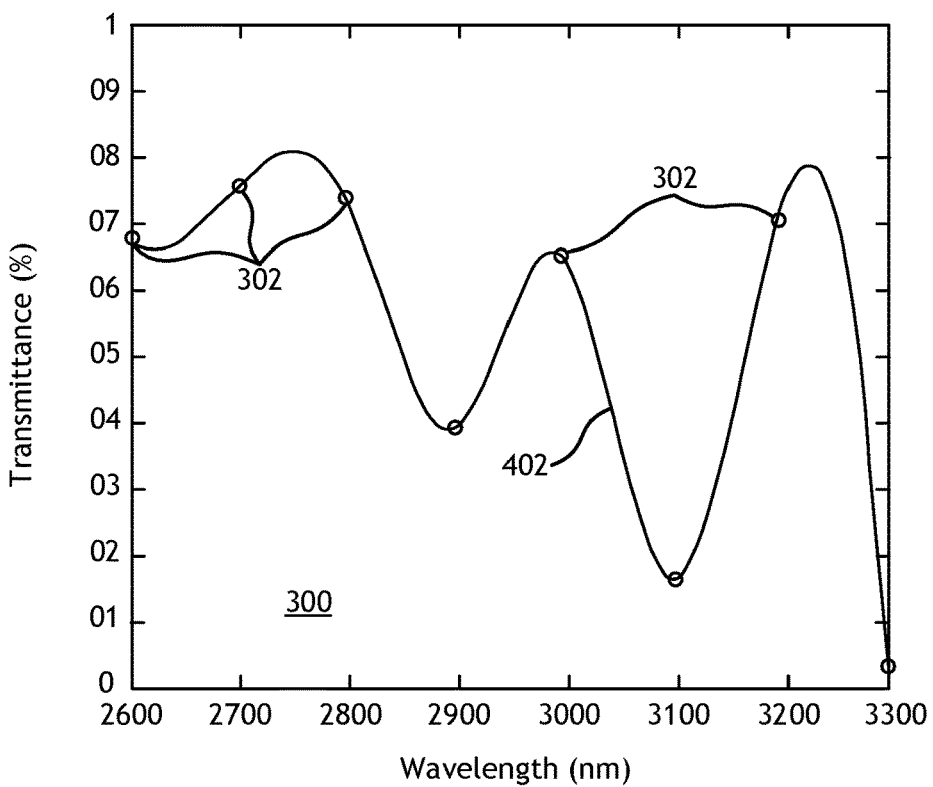
FIG. 4 depicts an example first transmission function fitted to the array of discrete data points of FIG. 3 initially projected onto the plot of FIG. 3.

Referring again to FIG. 2, the method 200 may then proceed by generating a line shape that connects to and is constrained by the array of discrete data points, and thereby generating a first transmission function, as at 204. The first transmission function extends over the predetermined wavelength region and is constrained by the values of the random data points 302 (FIG. 3). FIG. 4 depicts an example first transmission function 402 fitted to the array of discrete data points 302 initially projected onto the plot 300, as per 202. In some embodiments, as illustrated, the first transmission function 402 may comprise a polynomial line function. In other embodiments, however, the first transmission function 402 may comprise a square or linear line function, without departing from the scope of the disclosure.

The first transmission function 402 may be generated using a computer-operated point-by-point line interpolant process. In some embodiments, the point-by-point line interpolant process may comprise a spline function, such as a basis spline (B-spline) function, which may be operated using MATLAB® or a similar software program having instructions capable of being executed by a computer. The B-spline function provides a piecewise polynomial form of a cubic spline interpolant to the values of each data point 302 at the corresponding data sites.

Referring again to FIG. 2, the method 200 may then proceed by iteratively modifying the discrete data points of the first transmission function based on one or more performance criteria to generate a second transmission function, as at 206. As indicated above, example performance criteria can include, but are not limited to, SEC (accuracy), standard error of prediction (SEP), calibration sensitivity, transmission throughput, minimum prediction error, slope of the calibration curve, signal-to-noise ratio, environmental performance characteristics, predictive concentration range, linearity of prediction, thin-film stack thickness, individual layer thicknesses, mean transmission value, and variability of the above performance criteria as a function of temperature or fabrication tolerance.

Modifying the discrete data points of the first transmission function based on performance criteria may include iteratively altering the transmittance value (magnitude) of each discrete data point to optimize the performance criteria in view of a known or measured analyte concentration for a desired characteristic of interest. Also, modifying the discrete data points of the first transmission function based on performance criteria may include iteratively altering the location of each discrete data point along the predetermined wavelength region to optimize the performance criteria in view of the known analyte concentration of the desired characteristic of interest. In addition, modifying the discrete data points of the first transmission function based on performance criteria may include iteratively altering both the magnitude of the transmittance and the location of each discrete data point along the predetermined wavelength region.

Figure 5:
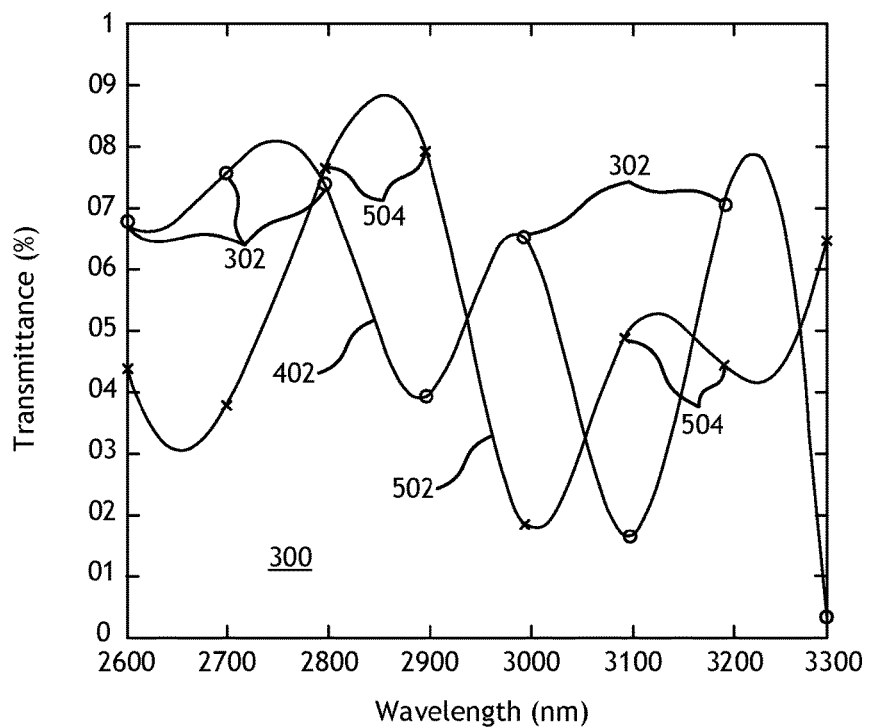
FIG. 5 depicts the plot of FIG. 3 showing the first transmission function in contrast with a second transmission function resulting from modifying the discrete data points based on one or more performance criteria.

FIG. 5 depicts the plot 300 showing the first transmission function 402 and a second or "target" transmission function 502 that results from modifying the discrete data points 302 based on one or more performance criteria, as at 206 (FIG. 2). Modifying the discrete data points 302 results in the generation of an array of new discrete data points 504. Each new discrete data point 504 is an iteration or variation of a corresponding one of the first discrete data points 302 and is based on the optimization (i.e., minimization or maximization) of one or more performance criteria. For instance, the discrete data points 302 of the first transmission function 402 may be modified by minimizing the SEC (accuracy) in view of a known or measured analyte concentration of a desired characteristic of interest. Also, the discrete data points 302 of the first transmission function 402 may be modified by maximizing the sensitivity in view of a known or measured analyte concentration of the desired characteristic of interest over the given analyte concentration range.

Once the discrete data points 302 are iteratively modified to provide the new discrete data points 504, a line shape may be generated that connects to and is constrained by the array of new discrete data points 504, and thereby generating the second transmission function 502. As with the first transmission function 302, the second transmission function 502 may be generated using a computer-operated point-by-point line interpolant process, such as a B-spline function. The second transmission function 502 may then be projected against an optical data set corresponding to a known or measured analyte concentration of the characteristic of interest such that the performance criteria may again be measured. This process may iteratively repeat until the performance criteria of the new discrete data points 504 and the associated second transmission function 502 reach a predetermined threshold. In some cases, for example, the process may iteratively repeat until the new discrete data points 504 and the associated second transmission function 502 reach a reasonable SEC or sensitivity threshold.

In cases where SEC is calculated, a second transmission function 502 exhibiting an SEC of 2.00 or less, for example, may be considered "predictive" or "viable" and a second transmission function 502 exhibiting an SEC of greater than 2.00 may be considered "non-predictive." The SEC threshold value that determines whether the second transmission function 502 is considered predictive or non-predictive, however, may be greater or less than 2.00, without departing from the scope of the disclosure. Moreover, it will further be appreciated that any performance criteria mentioned herein may equally have a corresponding minimum or maximum performance threshold that the second transmission function 502 may be measured against to determine if it is predictive or not.

Referring again to FIG. 2, the method 200 may then proceed by fitting a model transmission function for a model ICE design to the second transmission function and thereby identifying a predictive ICE design for the desired characteristic of interest, as at 208. Commercial software packages and/or stand-alone software capable of calculating transmission functions for given thin film stacks can be used to solve the Fresnel equations required to find a model ICE design having a given number of layers (i.e., layers 102 and 104 of FIG. 1) and layer thicknesses that exhibit a transmission function that most closely matches the optimized second transmission function over the predetermined wavelength range. In other words, fitting the model transmission function for the model ICE design to the second transmission function, as at 208, may comprise undertaking a portion of the forward design process generally described above. However, since the second transmission function 502 (FIG. 5) is already known, fitting the model transmission function for the model ICE design to the second transmission function 502 is much simpler and more efficient since it is not required to search for both an unknown ICE transmission function and a model ICE design film stack, as per the true forward design process.

Figure 6:
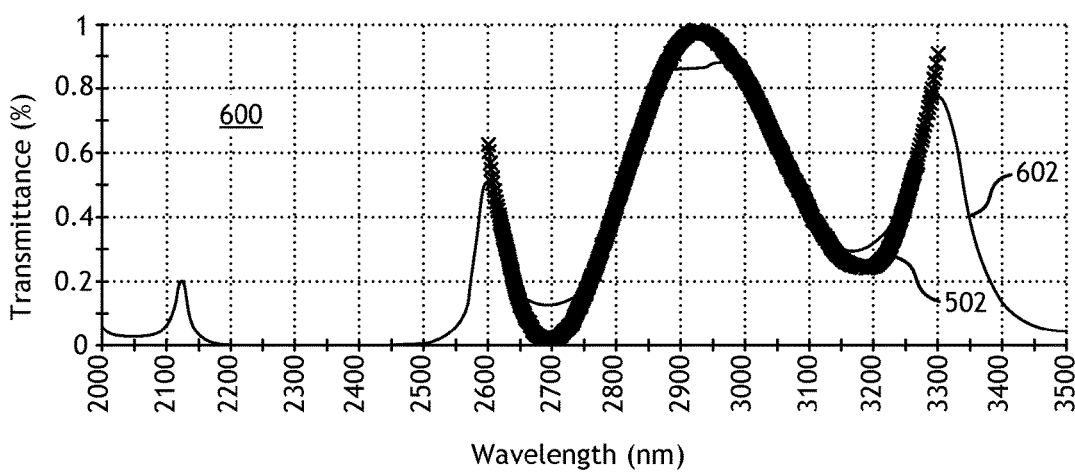
FIG. 6 is a transmittance versus wavelength plot depicting a model transmission function for an exemplary model integrated computational element design fitted against the second transmission function of FIG. 5.

FIG. 6 is a transmittance versus wavelength plot 600 depicting a model transmission function 602 for an exemplary model ICE design fitted against the optimized second transmission function 502 of FIG. 5. Fitting the model transmission function 602 of the model ICE design to the second transmission function may require the generation of the model ICE design using a computer-based software program. The software program commences the design process for the model ICE design by generating a random ICE design having a random number of layers (i.e., layers 102, 104 of FIG. 1) and/or a random thickness for each layer. The resulting random ICE design yields the model transmission function 602, and the software program may then iteratively modify the random ICE design in an attempt to alter the model transmission function 602 so that is more closely aligns with the second transmission function 502. Such modifications of the random ICE design includes varying layer optical thicknesses and/or adding or removing layers to the thin film stack. The software program repeats this process until the model transmission function 602 matches or closely matches the second transmission function 502, at which point the model ICE design may be considered a predictive ICE design for the desired characteristic of interest.

Once a model ICE design is determined to be a predictive ICE design, the model ICE design may be loaded into a fabrication computer program configured to instruct an associated fabrication machine or module to physically manufacture a thin film stack corresponding to the model ICE design. The fabrication computer program may be configured to receive and/or download the specifications for the model ICE design from the software program and instruct the fabrication machine to physically create a corresponding ICE by methodically or sequentially depositing the various layers of the ICE to the specified layer thicknesses.

The foregoing reverse design process provided by the method 200 of FIG. 2 was compared against the forward design process described above and the resulting predictive ICE designs from each design methodology were compared. Table 1 below, for example, shows a comparison of predictive ICE designs generated through the forward design and reverse design processes for six characteristics of interest: gas-to-oil ratio (GOR), methane ($C_1$), ethane ($C_2$), propane ($C_3$), saturates, and carbon dioxide ($CO_2$).

TABLE 1

| Predictive ICE | Sensitivity | |
| --- | --- | --- |
| Design | Forward Design | Reverse Design |
| GOR | 3.40E−05 | 4.30E−05 |
| $C_1$ | 10.36 | 10.9 |
| $C_2$ | 48 | 65.8 |
| $C_3$ | 36.2 | 47.9 |
| Saturates | 3.4 | 6.4 |
| $CO_2$ | 71.2 | 114.8 |

The predictive ICE designs for each design methodology were optimized with respect to sensitivity. As noted above, sensitivity can be determined by determining the detector response for the given ICE transmission function and then plotting this detector response vs. the analyte concentration. The slope of this plot determines the sensitivity, and the ICE is designed with the aim of maximizing this slope. For all six characteristics of interest, the predictive ICE designs generated using the reverse ICE design process were found to be more sensitive and were determined (found) significantly faster as compared to the predictive ICE designs generated using the forward ICE design process.

The ICEs designed as described herein may be useful in monitoring or otherwise detecting various analytes or characteristics of substances related to the oil and gas industry. For instance, the ICEs may be used in conjunction with an optical computing device to monitor and detect hydrocarbons, drilling fluids, completion fluids, treatment fluids, etc. The optical computing devices may be used in a downhole environment, such as within a wellbore or a tubular extended within the wellbore, or at a surface location, such as a rig floor, a monitoring facility adjacent a rig floor, or a remote location where a sample may be delivered for processing.

The methods described herein, or large portions thereof, may be automated at some point such that a computerized system may be programmed to design, predict, and fabricate ICEs that are more robust for fluctuating extreme environments. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. Also, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. Such code may be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the described embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A method for designing an integrated computational element (ICE) that includes generating an array of discrete data points and plotting the discrete data points across a predetermined wavelength region, generating a line shape that connects to and is constrained by the array of discrete data points, and thereby generating a first transmission function, iteratively modifying the discrete data points based on one or more performance criteria to generate a second transmission function, and fitting a model transmission function corresponding to a model ICE design to the second transmission function and thereby identifying a predictive ICE design configured to detect a desired characteristic of interest.

B. A non-transitory, computer readable medium programmed with computer executable instructions that, when executed by a processor of a computer unit, perform the method of generating an array of discrete data points and plotting the discrete data points across a predetermined wavelength region, generating a line shape that connects to and is constrained by the array of discrete data points, and thereby generating a first transmission function, iteratively modifying the discrete data points based on one or more performance criteria to generate a second transmission function, and fitting a model transmission function corresponding to a model ICE design to the second transmission function and thereby identifying a predictive ICE design configured to detect a desired characteristic of interest.

Each of embodiments A and B may have one or more of the following additional elements in any combination: Element 1: wherein the predetermined wavelength region corresponds to a wavelength range where the desired characteristic of interest is detectable. Element 2: wherein plotting the discrete data points across the predetermined wavelength region further comprises assigning a transmittance value to each discrete data point between zero and 1. Element 3: further comprising generating the array of discrete data points using a computer-operated random number generator. Element 4: further comprising randomly assigning a transmittance value to each discrete data point between zero and 1 with the random number generator. Element 5: wherein generating the array of discrete data points comprises calculating a predetermined regression vector corresponding to the characteristic of interest, and selecting critical point values from the predetermined regression vector, wherein the critical point values are used as the discrete data points. Element 6: further comprising generating one or both of the first and second transmission functions using a computer-operated point-by-point line interpolant process. Element 7: wherein iteratively modifying the discrete data points based on one or more performance criteria comprises at least one of determining a standard error of calibration of the second transmission function in view of the desired characteristic of interest, and determining an output sensitivity of the second transmission function in view of the desired characteristic of interest. Element 8: wherein iteratively modifying the discrete data points comprises at least one of iteratively altering a transmittance value of each discrete data point to optimize the one or more performance criteria in view of the desired characteristic of interest, and iteratively altering a location of each discrete data point along the predetermined wavelength region to optimize the one or more performance criteria in view of the desired characteristic of interest. Element 9: wherein fitting the model transmission function corresponding to the model ICE design to the second transmission function comprises generating with a computer the model ICE design having at least one of a random number of layers and a random thickness for each layer, iteratively modifying the model ICE design until the model transmission function aligns with the second transmission function, and identifying the predictive ICE design once the model transmission function aligns with the second transmission function. Element 10: wherein iteratively modifying the model ICE design comprises at least one of varying the thickness of one or more of the layers and varying the number of layers. Element 11: further comprising fabricating an ICE based on the predictive ICE design, and using the ICE in conjunction with an optical computing device to monitor a substance for a concentration of the characteristic of interest.

Element 12: wherein plotting the discrete data points across the predetermined wavelength region further comprises assigning a transmittance value to each discrete data point between zero and 1. Element 13: further comprising generating the array of discrete data points using a computer-operated random number generator. Element 14: wherein generating the array of discrete data points comprises calculating a predetermined regression vector corresponding to the characteristic of interest, and selecting critical point values from the predetermined regression vector, wherein the critical point values are used as the discrete data points. Element 15: further comprising generating one or both of the first and second transmission functions using a computer-operated point-by-point line interpolant process. Element 16: wherein iteratively modifying the discrete data points based on one or more performance criteria comprises at least one of determining a standard error of calibration of the second transmission function in view of the desired characteristic of interest, and determining an output sensitivity of the second transmission function in view of the desired characteristic of interest. Element 17: wherein iteratively modifying the discrete data points comprises at least one of iteratively altering a transmittance value of each discrete data point to optimize the one or more performance criteria in view of the desired characteristic of interest, and iteratively altering a location of each discrete data point along the predetermined wavelength region to optimize the one or more performance criteria in view of the desired characteristic of interest. Element 18: further comprising fabricating an ICE based on the predictive ICE design.

By way of non-limiting example, exemplary combinations applicable to A and B include: Element 3 with Element 4; Element 9 with Element 10; with Element 11.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method for fabricating an integrated computational element (ICE), comprising:
    generating an array of discrete data points and plotting the array of discrete data points across a predetermined wavelength region;
    generating a line shape that connects to and is constrained by the array of discrete data points, thereby generating a first transmission function;
    iteratively modifying the array of discrete data points based on one or more performance criteria to generate a second transmission function;
    fitting a model transmission function corresponding to a model ICE design to the second transmission function, thereby identifying a predictive ICE design configured to detect a characteristic of interest; and
    instructing an associated fabrication machine to physically manufacture the ICE based on the model ICE design.

2. The method of claim 1, wherein the predetermined wavelength region corresponds to a wavelength range wherein the characteristic of interest is detectable.

3. The method of claim 1, wherein plotting the array of discrete data points across the predetermined wavelength region further comprises assigning a transmittance value to each discrete data point between zero and 1.

4. The method of claim 1, further comprising generating the array of discrete data points using a random number generator.

5. The method of claim 4, further comprising randomly assigning a transmittance value to each discrete data point between zero and 1 with the random number generator.

6. The method of claim 1, wherein generating the array of discrete data points comprises:
    calculating a predetermined regression vector corresponding to the characteristic of interest; and
    selecting critical point values from the predetermined regression vector, wherein the critical point values are used as the array of discrete data points.

7. The method of claim 1, further comprising generating one or both of the first and second transmission functions using a computer-operated point-by-point line interpolant process.

8. The method of claim 1, wherein iteratively modifying the array of discrete data points based on one or more performance criteria comprises at least one of:
    determining a standard error of calibration of the second transmission function in view of the characteristic of interest; and
    determining an output sensitivity of the second transmission function in view of the characteristic of interest.

9. The method of claim 1, wherein iteratively modifying the array of discrete data points comprises at least one of:
    iteratively altering a transmittance value of each discrete data point to optimize a performance criterion in view of the characteristic of interest; and
    iteratively altering a location of each discrete data point along the predetermined wavelength region to optimize the performance criterion in view of the characteristic of interest.

10. The method of claim 1, wherein fitting the model transmission function corresponding to the model ICE design to the second transmission function comprises:
    generating with a computer the model ICE design having at least one of a number of layers and a random thickness for each layer;
    iteratively modifying the model ICE design until a model transmission function aligns with the second transmission function; and
    identifying the predictive ICE design once the model transmission function aligns with the second transmission function.

11. The method of claim 10, wherein iteratively modifying the model ICE design comprises at least one of varying a thickness of one or more of the layers and varying the number of layers.

12. The method of claim 1, further comprising using a transmittance function of the ICE to monitor a substance for a concentration of the characteristic of interest.

13. A non-transitory, computer readable medium programmed with computer executable instructions that, when executed by a processor of a computer unit, perform a method comprising:
    generating an array of discrete data points and plotting the array of discrete data points across a predetermined wavelength region;
    generating a line shape that connects to and is constrained by the array of discrete data points, thereby generating a first transmission function;
    iteratively modifying the array of discrete data points based on a performance criterion to generate a second transmission function;
    fitting a model transmission function corresponding to a model ICE design to the second transmission function, thereby identifying a predictive ICE design configured to detect a characteristic of interest; and
    instructing an associated fabrication machine to physically manufacture an ICE based on the model ICE design.

14. The non-transitory, computer readable medium of claim 13, wherein plotting the array of discrete data points across the predetermined wavelength region further comprises assigning a transmittance value to a discrete data point between zero and 1.

15. The non-transitory, computer readable medium of claim 13, further comprising generating the array of discrete data points using a computer-operated random number generator.

16. The non-transitory, computer readable medium of claim 13, wherein generating the array of discrete data points comprises:
calculating a predetermined regression vector corresponding to the characteristic of interest; and
selecting critical point values from the predetermined regression vector, wherein the critical point values are used in the array of discrete data points.

17. The non-transitory, computer readable medium of claim 13, further comprising generating one or both of the first and second transmission functions using a computer-operated point-by-point line interpolant process.

18. The non-transitory, computer readable medium of claim 13, wherein iteratively modifying the array of discrete data points based on one or more performance criteria comprises at least one of:
determining a standard error of calibration of the second transmission function in view of the characteristic of interest; and
determining an output sensitivity of the second transmission function in view of the characteristic of interest.

19. The non-transitory, computer readable medium of claim 13, wherein iteratively modifying the array of discrete data points comprises at least one of:
iteratively altering a transmittance value of a discrete data point to optimize the performance criterion in view of the characteristic of interest; and
iteratively altering a location of a discrete data point along the predetermined wavelength region to optimize the performance criterion in view of the characteristic of interest.

20. The non-transitory, computer readable medium of claim 13, further comprising instructions to monitor a substance for a concentration of the characteristic of interest with a transmittance function of the ICE.

* * * * *